United States Patent [19]
Bernard

[11] 4,294,258
[45] Oct. 13, 1981

[54] MEASURING HEAD ENABLING THE PRODUCTION OF PHYSIOLOGICAL MEASUREMENT SIGNALS DESIGNED TO BE POSITIONED ON OR IN CORPOREAL PARTS

[75] Inventor: Claude Bernard, Le Plessis-Robinson, France

[73] Assignee: Agence Nationale de Valorisation de la Recherche (Anvar), Neuilly-sur-Seine, France

[21] Appl. No.: 21,779

[22] Filed: Mar. 19, 1979

[30] Foreign Application Priority Data

Mar. 23, 1978 [FR] France .................. 78 08428

[51] Int. Cl.³ .......................... A61B 5/00; A61B 5/04
[52] U.S. Cl. .................. 128/635; 128/642; 204/195 B
[58] Field of Search .............. 128/635, 632, 642, 639; 204/195 B

[56] References Cited
U.S. PATENT DOCUMENTS

| | | | |
|---|---|---|---|
| 3,224,433 | 12/1965 | Dalebor | 128/635 |
| 3,800,784 | 4/1974 | Kiszel et al. | 128/642 |
| 3,804,080 | 4/1974 | Ruttgers et al. | 128/642 |
| 3,973,555 | 8/1976 | Moller et al. | 128/635 |
| 4,151,835 | 5/1979 | Showell et al. | 128/642 |

OTHER PUBLICATIONS

Huch et al., "Trancutaneous Measurement of Blood $PO_2$...," J. Pernat. Med. 1 (1973), 183.

*Primary Examiner*—Lee S. Cohen
*Attorney, Agent, or Firm*—Larson and Taylor

[57] ABSTRACT

The measuring head enables the production of measuring signals relating to electrical activity and measuring signals relating to an ionic or physico-chemical activity, notably pH, and is designed to be located on or in parts of a living body, notably on the head of an unborn infant. It comprises an insulating body bearing fastening claws. At the moment of positioning, the insulating body introduces actively an electrode sensitive to the electrical activity and at least one electrode sensitive to an ionic or physical activity. These electrodes are constructed in needle form, body body having also a reference electrode associated with the electrode sensitive to the ionic or physical activity.

32 Claims, 16 Drawing Figures

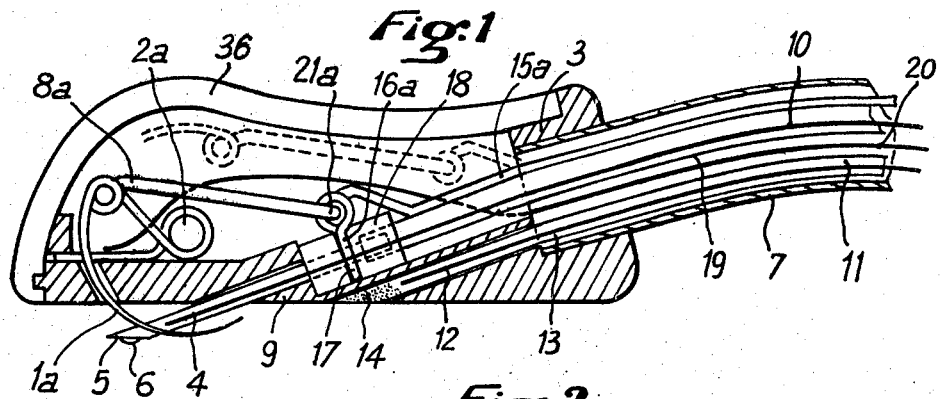
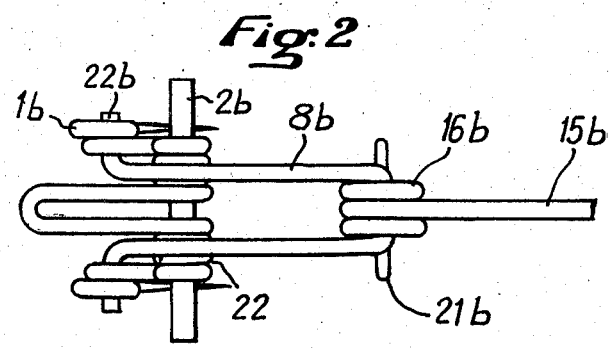
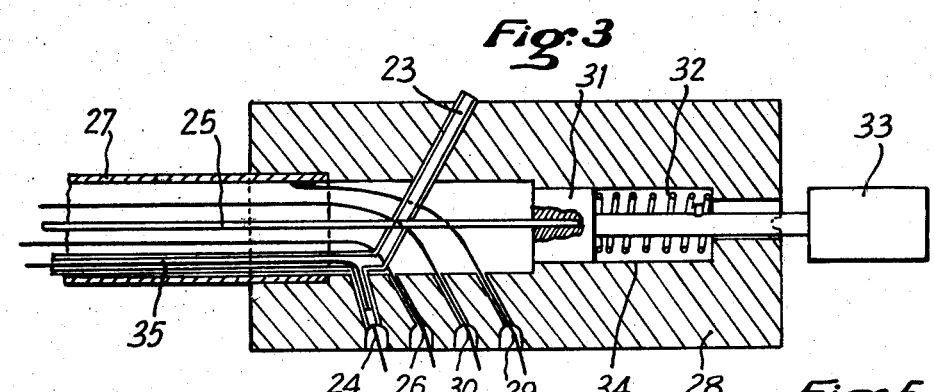
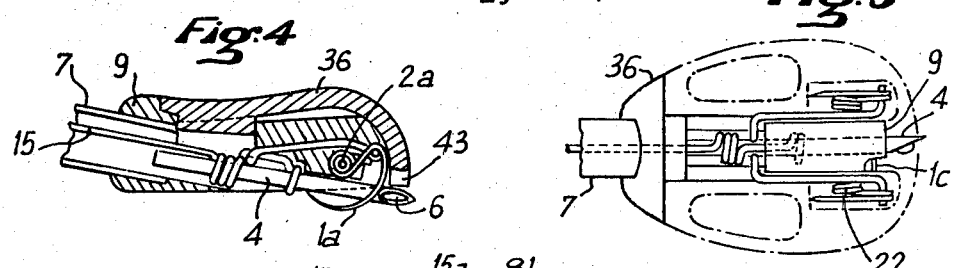
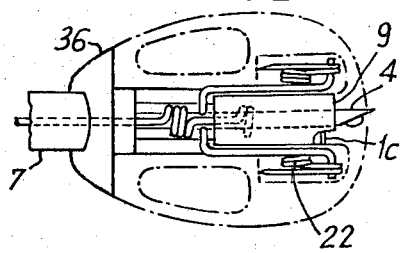
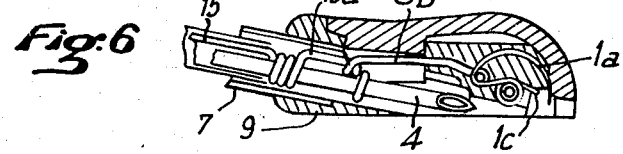

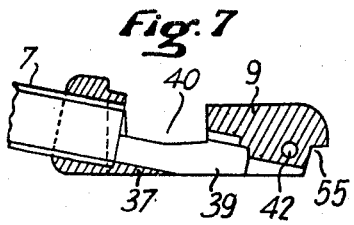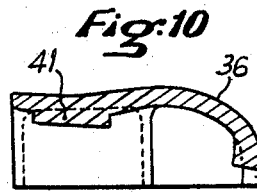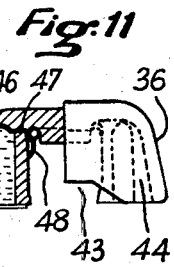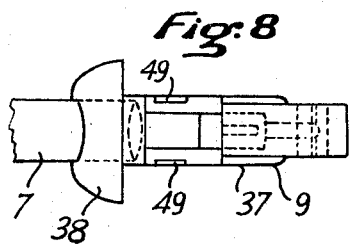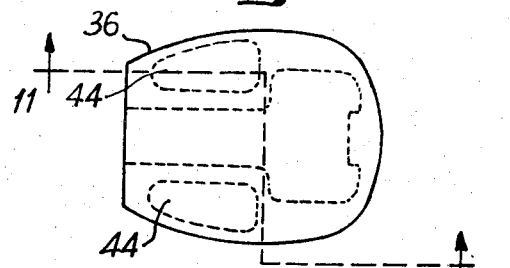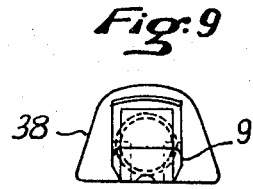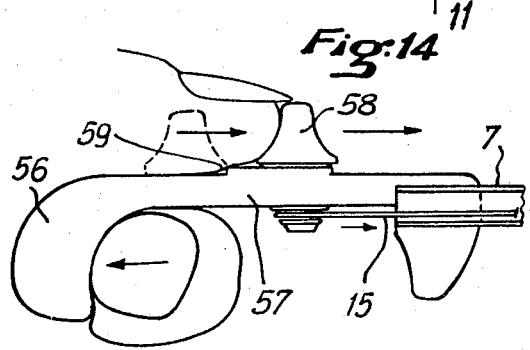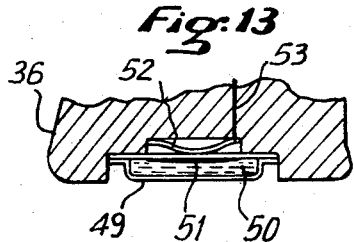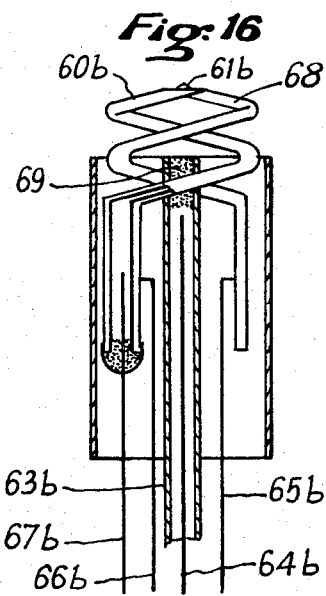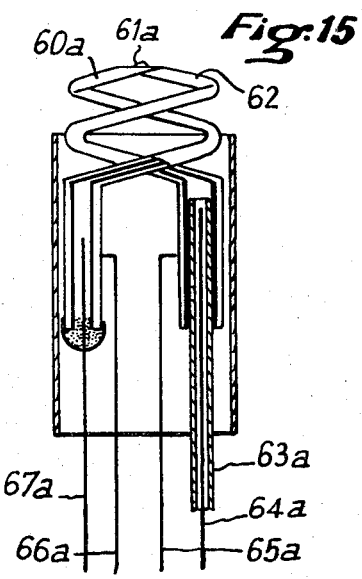

MEASURING HEAD ENABLING THE PRODUCTION OF PHYSIOLOGICAL MEASUREMENT SIGNALS DESIGNED TO BE POSITIONED ON OR IN CORPOREAL PARTS

The present invention relates to a combination measuring head, designed to be positioned on or in parts of the body, enabling the production of measuring signals relating to an electrical action or activity on the one hand, and to an ionic or physico-chemical action on the other hand.

It is known, to carry out measurements on unborn infants, to use a measuring head constituted by a spiral shaped double claw, with two sharp ends displaced by 180° with respect to one another, enabling an electrocardiograph signal to be taken, positioned concentrically with respect to a central electrode, constituted by a glass material sensitive to hydrogen ion activity and enabling the local tissue pH to be sampled. The whole is fixed to an insulating body.

This configuration presents a certain number of drawbacks. The first relates to its positioning technique. The latter is effected, in fact, in two stages: in a first stage, preliminary positioning of the spiral electrode which permits, in addition to the fixing of the whole of the measuring head to the part to which it is applied, the pick-up of the electrocardiographic signal.

The glass pH electrode, associated with its own reference electrode is then introduced through a central orifice, situated in the insulating body of the measuring head so that it is held in place. It is hence positioned only after the spiral electrode has been applied. The positioning of this type of measuring head requires, on the part of the user, complex and difficult manipulations which can disturb the patient.

The double spiral shaped claw requires also to be protected, by positioning accessories, notably to avoid injuring the patient during the introduction of the latter into the corporeal part.

The second drawback of this measuring head relates to its relative fragility. In fact, when it is placed on the "scalp" of the unborn infant, it may frequently happen that, as a result of movements of sufficiently great amplitude of the latter, that it is placed in overhanging position and that, as a result of forces which are too great, the glass electrode becomes broken, and the spiral electrode claws become deformed. This is explained by the fact that the support surface of the measuring head is small with respect to its height, and also by the fact that its axis of symmetry, coinciding moreover with the incoming electrical leads, is perpendicular to the fixing surface.

The third drawback relates to the relative instability of the fixing of the measuring head. The latter is in fact fixed by means of the spiral shaped double claw which is introduced onto the skin by a helical rotary movement. Following the movements of the unborn infant, the measuring head has a tendency to perform by itself a reverse rotary movement, tending to disengage it from the skin. This disengagement of the fastening may have the effect of creating discontinuities in the signals supplied by the electrodes of the measuring head and, consequently, resulting in poor interpretation of the latter.

Another drawback arises from the fact that the reference electrode, associated with the pH measuring electrode, is most currently constituted by a silver-silver chloride wire dipping into a solution of KCl which must be kept in a container of sufficient capacity to be able to moisten the corporeal part in contact with the reference electrode during the whole time of measurement. This container, being situated in the body of the measuring head, consequently has a limited capacity, as well as access means, for its possible filling in the course of the measurement, difficult to reach.

Consequently, it appeared useful to provide a novel device, according to the present invention, enabling the above-said drawbacks to be eliminated and notably the positioning of the measuring head in a single operation, without the use of a positioning accessory and without risk of injuries during its positioning on the corporeal part.

It is also an object of the present invention to provide a novel measuring head construction which can, in spite of movements of considerable amplitude of the part where the measuring head is applied, withstand considerable forces, without deformation or breakage of all or a part of the latter.

It is also an object of the invention to provide a fastening for the masuring head which, inspite of these movements, is not releasable without external human intervention in order to avoid, consequently, discontinuities in the measuring signals and misinterpretation of the latter.

It is another object of the invention to provide a reference electrode, associated with the tissue ion activity measuring electrode, whose container is of large capacity, and whose filling orifice is easy to reach, even in the course of the measurement.

It is also an object of the invention to constitute a measuring head combination, enabling the simultaneous production of measuring signals relating to electrical action as well as to ionic action, or physico-chemical action, of the corporeal part where it is applied, and whose positioning is done in a single operation, without the use of a special protective accessory for the claw during the positioning and without risk of tearing the surface of the corporeal part, on or in which it is placed, during its introduction.

Another object of the invention is to produce a measuring head which, once positioned on or in the corporeal part, is mechanically stable, in spite of the movement of the part where the measuring head is applied, and which cannot be placed in overhanging position, following its movements, thus eliminating risks of breakage or deformation of the electrodes.

Another object of the invention is to construct a measuring head whose fastening device cannot be disengaged, without external human intervention, following movements of the part on which it is applied, in order to avoid the measuring signals being interrupted.

It is another object of the invention to provide a measuring head whose electrode, sensitive to ionic activity, forms an integral part of the mechanical fixing device of the latter to the corporeal part where it is applied, in association with the one or more electrodes sensitive to the electrical activity to be measured.

A further object of the invention is to provide a measuring head, having a reference electrode which can be KCl, whose container is of large capacity and is provided with a filling orifice easy of access, so that it can be fed from the outside, if necessary continuously, without, however, the outer dimensions of the measuring head being increased and without the measurement being interrupted.

Yet another object of the invention is to provide a measuring head, having a reference electrode which can be with KCl and which is easily replaceable.

GENERAL DESCRIPTION OF THE INVENTION

According to the invention there is therefore provided a measuring head enabling the production both, and preferably simultaneously, of physiological measuring signals, notably of measuring signals relating to an electrical activity, for example for an electrocardiogram (ECG) and of signals relating to ionic or physicochemical activity, preferably the pH, designed to be positioned on and/or in corporeal parts, notably on the skull of the unborn infant, said head comprising an insulating body bearing claw means which can serve as electrodes sensitive to the electrical activity, said measuring head being characterized by the fact that said insulating body presents actively, at the moment of positioning, said electrode sensitive to the electrical activity and at least one electrode sensitive to an ionic or physical activity, said electrodes being constructed in the form of semi-circular, spiral or linear needles, said body bearing also a reference electrode associated with the electrode sensitive to the ionic activity.

In a preferred embodiment of the measuring head according to the invention, said head has, as claw means, movable and retractable claws capable, by external actuation, of penetrating into the corporeal part against which the head is applied, said claws being preferably sensitive to the electrical activity, as well as at least one electrode sensitive to the ionic activity also movable and retractable. Particularly advantageously, said electrode sensitive to the ionic activity penetrates into the corresponding organ, for example, the scalp of the unborn child, with a very small angle of incidence with respect to the surface of said organ, the direction of penetration being preferably opposite the direction of the penetration of the movable and retractable claw-shaped electrodes. Particularly preferably, said movable and retractable claw and said electrode sensitive to the ionic activity are mechanically coupled so as to be simultaneously extended or retracted.

Advantageously, the insulating casing can have, at the level of the penetration zone of the electrode sensitive to the ionic or physical activity and/or of the claws, recesses causing the passage of a discontinuity in the curve of the skin surface, to facilitate the piercing of the skin and the fastening.

Still in this preferred embodiment, the measuring head according to the invention may advantageously include a flexible sheath of which one of the ends is placed in abutment on a corresponding end of the casing, the other end of the sheath including an adjusting means, said sheath surrounding a flexible extension of the body of said electrode sensitive to the ionic or physical activity as well as that of its associated reference electrode, the electrical leads of the measuring signals and a longilinear and flexible mechanical member transmitting to said movable and retractable electrodes the translation movement obtained by said adjusting means.

The associated reference electrode, which can be notably a KCl electrode, extends advantageously over the whole length of the sheath to form in this way an enlarged KCl container. This electrode is terminated advantageously at the level of the surface of the casing applied against the skin of the corresponding member, by a porous boundary means for the KCl, for example a porous ceramic or a tablet of suitable material.

In a specific embodiment, said casing may be provided with one or two discardable reference electrodes such as, for example, a gelled KCl plate protected by a porous coating, for example of paper. Again in a specific embodiment, the head can have a removable discardable cap, said cap having one or several KCl containers, as well as one or several associated electrical contacts and capable of being applied, at the moment of mounting the base, on a complementary contact presented by the receiver portion of the casing, the electrical transmission being effected through a suitable lead from this latter contact.

In order to facilitate, if necessary, replacement of the claw means, which are preferably curved claws urged by elastic means into inserted position and capable of being withdrawn, against said elastic means, by the external adjusting device, it is possible to provide for the casing to bear one or several metal pincers capable of receiving the fixed end of said claw means to ensure electrical continuity.

BRIEF DESCRIPTION OF THE DRAWINGS

Other features, advantages and characteristics of the invention will appear on reading the description which follows, given by way of non-limiting example, with reference to the accompanying drawing in which:

FIG. 1 shows diagrammatically a preferred embodiment of a measuring head according to the invention;

FIG. 2 shows the detail of a simple mechanism enabling the coupling of the movement of the electrode sensitive to the ionic action with the rotary movement of the claw;

FIG. 3 shows a diagrammatic view of an adjusting means for the head according to the invention;

FIG. 4 shows a sectional view of another embodiment of a measuring head according to the invention;

FIG. 5 shows a view from above of the embodiment of FIG. 4, the removable and discardable cap being shown in dot dash lines;

FIG. 6 shows a view similar to that of FIG. 4, but with the electrodes retracted;

FIGS. 7, 8 and 9 show lateral, overhead and end views, respectively of the base of a measuring head according to the invention;

FIGS. 10, 11 and 12 show views in lateral section, in half-section along line 11—11 of FIG. 12, and from above, of the removable cap;

FIG. 13 shows a partial view of the cap in an embodiment with a discardable reference electrode;

FIG. 14 shows a lateral view of external adjusting means;

FIG. 15 illustrates another embodiment of the invention; and

FIG. 16 shows also yet another embodiment of the invention.

DESCRIPTION OF PREFERRED EMBODIMENTS

In the embodiment illustrated in FIG. 1, the measuring head includes a single or double claw 1a, of semi-circular shape, movable around a horizontal axle 2a, parallel to the body surface where the measuring head is applied, which can emerge from or penetrate into the casing 3 forming the body of the measuring head, by a rotary movement and enabling the pick-up, when it is driven into the body part, of a signal derived from the electrical activity of the latter. The measuring head includes on the other hand, a selective electrode 4, sensitive to the hydrogen ion activity, formed by a fine stainless steel tube 5 with a beveled end, containing and protecting the selective electrode 4 proper and allowing the slight protrusion, on the side of the beveled end, of the sensitive diaphragm 6 which can be of glass. This electrode 4, rectilinear in shape, is given a linear translation movement, along an inclined axis coinciding with the axis of the hollow cylindrical sheath 7, itself coming into abutment with the casing 3 and extending between the two preceding claws 1a, at the level of the corporeal part.

The selective electrode 4 is advantageously a pH detection electrode of the usual commercially sold type. It is seen that the direction of penetration of this electrode is opposite the direction of penetration of the claws 1a, which ensures firm fastening of the measuring head.

A movable mechanical element 8a, coupling the selective electrode 4 to the double claw 1a, enables the translation movement of the first to be converted into a rotary movement of the second. This operation is done so that when the selective electrode 4 is pushed downwards into the corporeal part along a linear movement, the double claw 1a is also driven into this same corporeal part in a rotary movement, so that the claw 1a resists the disengagement of the selective electrode 4.

The selective electrode 4 is guided in its translation movement, on the side of the corporeal part, by the base 9 of the measuring head and, at its other end by the flexible sheath 7 which can be formed by means of a spiral steel wire, with contiguous turns. This flexible sheath 7, sufficiently rigid to protect the elements that it contains, surrounds the electrical cable 10 of the selective electrode 4, and surrounds the extension 11 of the container of the KCl reference electrode 12, which can be constituted by a fine polyethylene tube 13 terminating in a porous material 14, designed to limit the amount of KCl flowing from the reference electrode, and having a sufficient cross-section so that particles or bodies of biological origin do not come to obstruct it. The position of this orifice, as well as its cross section, are selected so as to ensure the best possible electrical contact between the corporeal part and the KCl reference electrode.

The flexible sheath 7 also surrounds the electrical lead 20 connected to the double claw 1a, as well as the mechanical element 15a, which can be a sufficiently rigid and flexible steel wire, fastened inside the casing 3 through a collar 16a which can be removable and gripped around the selective electrode 4, at the level of a groove 17 formed in the insulating ring 18 whose purpose is, moreover, to improve the quality of the junction formed between the rigid part 5 of the selective electrode 4 and its flexible extension which can be a polyethylene tube 19. The movable fastening axle 21a holds the gripping collar 16a, the movable mechanical element 8a and the movable mechanical element 15a, assembled together.

The part in dotted lines, representing the movable mechanical element 8a, corresponds to a position wherein the two types of electrodes are placed in retracted position, inside the casing. In this position, neither the semi-circular claw 1a, nor the needle electrode 4, can come into contact with the corporeal part.

FIG. 2 shows the details of a possible embodiment of a coordinating mechanism for the movements between the semi-circular claw shaped electrode 1b and the selective electrode 4, endowed with a linear translation movement. It comprises the movable mechanical element 8b, connected on the one hand to the movable fastening axle 21b, fast to the selective electrode 4 sensitive to the ionic activity, and on the other hand to the movable fastening axle 22b, fast to the claw 1b. The fixed fastening axle 2b is fast to the body of the measuring head. It can be surrounded by several turns 22, integral parts of the double claw 1b, which can play the part of a return spring, contributing, either to the introduction of the electrodes into the corporeal part, or to their retraction within the casing. The movement of the assembly is controlled by the element 15b through the collar 16b and the movable axle 21b.

FIG. 3 shows a possible arrangement of the adjusting means, placed at the other end of the flexible sheath 27, marked as 7 in FIG. 1. This adjusting means can be constituted by a body 28, of insulating material, also receiving an abutment the other end of the sheath 27. It contains a cylindrical cavity 34 intended to guide the other end 25 of the flexible rod, denoted as 15a, in FIG. 1. The latter is extended, inside, by a handle 33 and includes, in the cylinder 34, a return spring 32 as well as a ring 31 which is fast to it. This spring, abutting against the ring 31 and against the body of the casing 28 permits, by the pressure that it exerts on the cable 25, the holding of the two electrodes, denoted as 1a and 4 in FIG. 1, in penetrated position, and, consequently, to hold the measuring head fastened to the corporeal part to which it is applied. It is possible, without departing from the scope of the invention, to contemplate any other adjusting means for the position of the electrodes.

The casing 28 holds moreover the two electrical leads 29 and 30 supplying the signal relating to the electrical activity of the corporeal part. The lead 30 is connected to the semi-circular double claw. The lead 29 is shown here electrically connected to the metal sheath 27. It could be formed otherwise, the essential thing being that it is connected to the reference electrode associated with the one or more claws enabling the signal to be obtained relating to the electrical activity of the corporeal part. The casing also holds the electrical leads 24 and 26. The lead 26 is the extension of the internal lead from the sensitive selective electrode. The lead 24 is the extension of the inner lead of the KCl reference electrode associated with the selective electrode. It is to be noted that this lead can replace the lead 29 and serve, for the signal relating to the electrical activity, as reference electrical lead.

The reference electrode 35 is terminated, within the casing 28, by a double branch, one containing the electrical lead 24, the other the filling orifice 23. This orifice may be most simply constituted by the extension of the polyethylene tube, constituting the extension of the body of this same KCl reference electrode, or by any other device enabling the filling of the latter with KCl, continuously or not, during the measurement or not, without departing from the scope of the invention.

In the description given in the FIGS. 1, 2 and 3, the whole of the measuring head is used by placing in one hand, the casing containing the fastening electrodes, the index being placed on the latter, in a hollow provided for this purpose, so as to direct the latter by "touch" within the corporeal part.

The other end of the measuring head 28 is held in the other hand taking care, during positioning, to maintain the handle 33 of FIG. 5 pulled and, consequently, to keep retracted, within their casing, the fastening electrodes in order not to injure the corporeal part during positioning. The position of the measuring head on the corporeal part having been selected, it suffices, whilst holding it in position, to release the handle 33 connected to the cable 25 which, under the reaction of the spring 32 which was in compressed position pushing the ring 31 fixed to the cable 25, has the effect of advancing the selective electrode 4 of FIG. 1 into the corporeal part, as well as the claws 1a shown in the same figure. To withdraw the electrode from the corporeal part, the reverse operation must be followed.

Reference will now be made to FIGS. 4 to 12 in which homologous elements bear the same reference numerals. The base 9 of the head receives, removably, a cap or cover 36. The form of the base is seen in FIGS. 7 to 9. It includes a rectilinear part 37 with an enlarged rear end 38 having substantially the width of the cap 36 and the base is traversed by an orifice slightly inclined with respect to its inner surface 39, being enlarged in zone 38 to enable the insertion and fixing by locking of the end of the flexible sheath 7. In front of the widened part 38, the base 9 has an upper recess 40 communicating with the orifice 39 and whose edges approach one another slightly to permit the fastening by clipping of the cover 36 having for this purpose a suitable relief 41.

The base 9 still has towards its front part a transverse 42 for the passage of the axle 2a.

A cap or cover 36 has the shape shown in FIGS. 10 to 12, this substantially semi-ovoid shape having, at the front end, a groove 43. When the head of the device is applied to the skin of the unborn infant, the skin has a tendency to project all around the head and this relief tends to penetrate into the notch 43. This is thus favorable to the penetration of the end of the electrode-needle 4 into the skin. It is also possible, if desired, to create notches laterally to facilitate the penetration of the claws 1a.

The reference electrode may advantageously be replaced, by providing in the cover 36 two vertical blind orifices 44 opening at the lower surface. It is seen, in FIGS. 11 and 12, that the shape of these orifices is elongated parallel to the axis of the head. These orifices may be closed at their lower surface by a porous film 45, for example of paper. The orifice 44 is replaced by a KCl paste or the like, for example based on agar-agar. The bottom of the orifice is lined with a conductive film of silver and silver chloride 46 connected by a lead 47 to a small strip contact 48 situated on the inner surface of the inner wall of the orifice 44. The lead 47 passes through this wall. The contact strips 48 are applicable against corresponding metal strips 49 housed in lateral recesses of the part 37 of the base 9 to ensure electrical contact. The two contacts 49 are connected to a lead 10 (shown only in FIG. 1).

The contacts 48, 49 may be situated at other places of the base or of the cover shielded from amniotic liquid.

In a modified embodiment, it is possible to envisage a discardable cover similar to cover 36, but without the presence of the orifices 44. It would suffice to provide, at the places occupied by the two films 45 housings capable of receiving removably reference electrode forming tablets and containing, from below to above, a porous film 49 of paper, a layer of potassium chloride paste 50, a conducting tablet 51 of silver/silver chloride, said silver tablet coming into contact with a metal contact part 52 present at the bottom of the recess and connected at 53. Such an embodiment can be seen in FIG. 13.

The connection between the needle-electrode 4 and the flexible control element 15, for example a steel wire, is effected preferably as is seen in FIGS. 4 to 6, by winding the element 15 around the needle 4 so as to form, between two successive turns, a strand separated laterally 15a enabling the hooking of the element 8b. The claws 1a themselves are formed from a single spring steel wire whose two ends are curved back into the form of claws 1a, said claws being extended by a certain number of turns 22 arranged around the axle 2a, said groups of turns being connected by a central strand 1c. It is seen that this central strand passes into a dihedral angle 55 situated at the front part of the base 9. In order to enable easy replacement of the part constituted by the claws 1a, the windings providing spring function 22 and the central strand 1c, it is possible to provide, in this dihedral angle, a metal pincer (not shown) into which the strand 1c becomes removably engaged to be gripped by this pincer. The pincer is connected to the electrical lead 20 to transmit the electrical signals detected by the claws 1a.

Referring to FIG. 14, there is seen a control device provided at the outer end of the sheath 7 and playing a similar role to the device shown in FIG. 3. This device provides a control handle 56 against which the index finger of the operator can be placed. This handle is extended by a rectilinear part 57 provided with a central slot in which a sliding knob 58 capable of being moved by the thumb is slideably guided. On this knob 58 is fastened the end of the flexible element 15. It is seen that the upper surface of the extension 57 has a rear shoulder 59 forming a stop. Normally, the claws 1a are in the position shown in FIG. 6 and, under these conditions, the part 8b is in its rear position, the electrode 4 not emerging from the lower base of the measuring head. The finger 58 is then in a rear position, in which position it is held in abutment, in the position shown in dashed lines, against the stop 59. From this position the operator, having introduced the measuring head into the neck of the uterus and applied the base of said head against the cranial skin of the still unborn child, lifts the knob 58 which is thus disengaged from the stop 59. The turns 22 then push back the claws 1a into active position shown in FIG. 4 and, in this movement, the part 8b transmits a traction force to the element 15 which causes the driving of the electrode 4 into its position shown in FIG. 4 and also the forward movement of the knob 58. The knob has then reached the forward position shown in FIG. 14. To retract the claws and the electrode 4, the user pushes back the knob 58 with the thumb rearwards to bring it back into the position shown in dashed lines.

If necessary, if the force of the turns 22 is insufficient, the user may, by thrusting against the knob 58 to push it back forwards, aid in the perforation of the cutaneous wall by the claws 1a.

In another modification the claws 1a may not serve as electrodes and it is then the metal tube 5 of the electrode 4 which, connected to a lead, for example the flexible rod 15, detects the electrocardiographic signals. In all cases it is possible to provide a counter electrode ECG on the sheath, coming into contact with a maternal corporeal part.

Another possible embodiment of the measuring head according to the invention, only including a part of the advantages of the above description, is shown in FIG. 15 as well as in FIG. 16.

FIG. 15 takes up the double spiral electrode embodiment. Each claw is electrically insulated from the other and is formed by means of a spiral shaped steel tube of which one end, positioned in the corporeal part, is cut into a bevel. The hollow claw 60a contains and protects the selective electrode whose diaphragm, sensitive to ionic activity, appears at 61a. The second hollow claw 62 contains the extension of the KCl electrode, extended outwards by a member which can be constituted by a flexible polyethylene tube 63a and having the same advantages as those described in the preceding embodiment. The sets of electrical leads 65a and 64a for claw 62 and 66a and 67a for the other claw 60a are insulated from one another, and can pick up the electrical signal relating to the electrical activity of the corporeal part. The electrical leads 64a and 65a enable the pick-up of the measuring signal relating to ionic activity.

FIG. 16 shows a modification of the embodiment of FIG. 15, in the sense where the KCl reference electrode is no longer introduced into the corporeal part by means of the hollow claw 68, but becomes exposed under the base of the insulating material of the measuring head, creating an electrical contact 69 at the level of the corporeal surface and having an electrical lead 64b. These two latter versions no longer include electrode retraction means. Claw 68, with tip 61b, includes electrical lead 65b, while the other claw 60b includes electrical leads 66b and 67b.

I claim:

1. A measuring head adapted to be positioned on or in corporeal parts of a living body, said head comprising:
   an insulating body,
   said insulating body having a first electrode means which is sensitive to electrical activity of said corporeal parts, an electrical lead operatively connected to and extending from said first electrode means,
   said insulating body also having a second electrode means which is sensitive to an ionic or physical activity of said corporeal parts, an electrical lead operatively connected to and extending from said second electrode means,
   an elongated sheath means being connected to and extending from said insulating body, said electrical leads extending from the insulating body along said sheath means,
   said insulating body having a claw means movable between a retracted position within said insulating body and an extended position out of said insulating body whereat it is positioned to enter the corporeal parts, to thereby secure the measuring head to the corporeal parts,
   control means for moving the claw means between said retracted and extended positions such that in the said extended position the claw means has entered the corporeal parts while said first and second electrode means simultaneously engage the corporeal parts.

2. A measuring head according to claim 1 wherein said first electrode means comprises the claw means and said second electrode means comprises a selective electrode having a needle form and being mechanically connected to said claw means to be movable between a retracted position in said insulating body and an extended position into said corporeal parts.

3. A measuring head according to claim 2 wherein said claw means and said selective electrode are mechanically coupled to each other so as to be simultaneously extended or retracted relative to the insulating body.

4. A measuring head according to claim 2 wherein said selective electrode comprises an electrically conductive outer member forming an electrode forming part of said first electrode means.

5. A measuring head according to claim 4 including an electrically conductive flexible rod located in said sheath means and wherein said conductive outer member is electrically connected to said rod, said rod forming a part of said control means for transmitting movements to both said claw means and said selective electrode.

6. A measuring head according to claim 2 wherein said second electrode means further comprises a reference electrode borne by said insulating body and having a substantial surface for contact engagement with said corporeal parts.

7. A measuring head according to claim 2 wherein said selective electrode is inclined with respect to said insulating body to penetrate into said corporeal parts with its axis slightly inclined with respect to said corporeal parts.

8. A measuring head according to claim 7 wherein said insulating body includes a cap adapted to be urged against said corporeal parts, said cap having, at the level where said second electrode means penetrates said corporeal parts, a recess allowing the passage of a discontinuity in the curvature of the skin produced by a base portion of the insulating body which engages the skin, in order to facilitate the piercing of the skin.

9. A measuring head according to claim 2 wherein said claw means and said selective electrode are positioned in the insulating body to penetrate in said corporeal parts following directions approaching one another.

10. A measuring head according to claim 1, wherein the claw means from the first electrode means which is sensitive to the electrical activity.

11. A measuring head according to claim 1, wherein the said second electrode means sensitive to the ionic activity also comprises means sensitive to the electrical activity to form the first electrode means.

12. A measuring head according to claim 1 wherein said claw means are constructed in the form of semi-circular needles forming the two ends of a metal wire member.

13. A measuring head according to claim 12 wherein said wire member includes spring forming turns.

14. A measuring head according to claim 12 wherein said needles are connected to said electrical lead and form part of said first electrode means.

15. A measuring head according to claim 12 wherein said insulating body comprises an elongated base traversed by an orifice slightly inclined with respect of the bottom part of said base and opening in said bottom part to slideably receive said second electrode means, said second electrode means comprising a slidable selective electrode, said base comprising means to receive said metal wire member, said base being covered by a substantially semi-ovoid cap.

16. A measuring head according to claim 15 including means for mechanically coupling said metal wire member and said slideable selective electrode so as to be simultaneously extended or retracted.

17. A measuring head according to claim 16 wherein said claw means form an electrode of said first electrode means.

18. A measuring head according to claim 1, said second electrode means having a flexible extension, and wherein said elongated sheath means is flexible and surrounds said flexible extension, said control means comprising a rectilinear and flexible mechanical member operatively connected to the claw means to transmit to said claw means a translation movement in response to movement of a regulating means which is located at the end of said sheath means remote from said insulating body.

19. A measuring head according to claim 18 wherein said second electrode means comprise a selective electrode and an associated reference electrode having a tubular body and a tubular extension of said tubular body in said sheath means to provide an enlarged container, said tubular extension having a filling orifice at said remote end of said sheath means.

20. A measuring head according to claim 18 wherein said regulating means comprise a handle mounting a slideable knob connected to said mechanical member and comprising stop means to hold said knob in a position where said claw means are in their retracted position.

21. A measuring head according to claim 1 wherein said second electrode means comprise a selective electrode and an associated disposable reference electrode removably fixed under said insulating body.

22. A measuring head according to claim 1 wherein said insulating body comprises a disposable head cap removably fixed on a base, and said second electrode means comprise a selective electrode and an associated reference electrode borne by said disposable head cap.

23. A measuring head according to claim 1 wherein said claw means form at least one electrode of said first electrode means.

24. A measuring head according to claim 1 wherein said first electrode means has a needle form and is mechanically connected to said claw means to be movable between a retracted position in said insulating body and an extended position into said corporeal parts.

25. A measuring head according to claim 24 wherein said first electrode means having a needle form further comprises a selective electrode of said second electrode means.

26. A measuring head according to claim 25 wherein said first electrode means having a needle form comprises an electrically conductive outer member forming an electrode forming part of said first electrode means.

27. A measuring head according to claim 26 including an electrically conductive flexible rod located in said sheath means and wherein said conductive outer member is electrically connected to said rod, said rod forming a part of said control means for transmitting movements to both said claw means and said first electrode means having a needle form.

28. A measuring head according to claim 25 wherein said claw means and said first electrode means are positioned in the insulating body to penetrate in said corporeal parts following directions approaching each other.

29. A measuring head according to claim 24 wherein said claw means and said first electrode means having a needle form are mechanically coupled to each other so as to be simultaneously extended or retracted relative to the insulating body.

30. A measuring head according to claim 24 wherein said first electrode means is inclined with respect to said insulating body to penetrate into said corporeal parts with its axis slightly inclined with respect to said corporeal parts.

31. A measuring head according to claim 30 wherein said insulating body includes a cap adapted to be urged against said corporeal parts, said cap having, at the level where said second electrode means penetrates said corporeal parts, a recess allowing the passage of a discontinuity in the curvature of the skin produced by a base portion of the insulating body which engages the skin, in order to facilitate the piercing of the skin.

32. A measuring head adapted to be positioned on or in corporeal parts of a living body, said head comprising an ovoid insulating body having an elongated base with a flare bottom part, said base being traversed by an orifice slightly inclined with respect of said bottom part, a reciprocating electrode means slideably received in said orifice, said electrode means being sensitive to an ionic or physical activity of said corporeal parts, said electrode means having a needle form and being provided with an outer tubular conductive member which is sensitive to the electrical activity of said corporeal parts, electrical lead means for said electrode means, a removable ovoid cap on said base, at least one curved needle forming a claw mounted on said body, an elongated sheath means connected to said insulating body and surrounding said electrical lead means, and means, including an elongated mechanical member movable in said elongated sheath means extending from said base, and operatively connected to the claw, for moving said electrical means and said at least one claw between a retracted position in said body and an extended position wherein they penetrate into said corporeal parts following directions approaching one another.

* * * * *